(12) United States Patent
Wen et al.

(10) Patent No.: US 9,623,077 B2
(45) Date of Patent: Apr. 18, 2017

(54) USE OF PEPTIDE FOR ALLEVIATING PAIN

(71) Applicants: Academia Sinica, Taipei (TW); National Sun Yat-sen University, Kaohsiung (TW)

(72) Inventors: Zhi-Hong Wen, Kaohsiung (TW); Jyh-Yih Chen, Ilan (TW)

(73) Assignees: ACADEMIA SINICA, Taipei (TW); NATIONAL SUN YAT-SEN UNIVERSITY, Kaohsiung (TW)

( * ) Notice: Subject to any disclaimer, the term of this patent is extended or adjusted under 35 U.S.C. 154(b) by 70 days.

(21) Appl. No.: 14/723,914

(22) Filed: May 28, 2015

(65) Prior Publication Data

US 2016/0346348 A1 Dec. 1, 2016

(51) Int. Cl.
*A61K 38/00* (2006.01)
*A61K 38/16* (2006.01)
*C07K 14/00* (2006.01)
*A61K 38/17* (2006.01)

(52) U.S. Cl.
CPC .................. *A61K 38/1706* (2013.01)

(58) Field of Classification Search
None
See application file for complete search history.

(56) References Cited

PUBLICATIONS

Scholz et al (2002). Nature Neuroscience. 5(Supplement):1062-1067.*
Wu-Fu Chen et al., The use of the antimicrobial peptide piscidin (PCD)-1 as a novel anti-nociceptive agent, 2015.

* cited by examiner

*Primary Examiner* — Christine J Saoud
*Assistant Examiner* — Jon M Lockard
(74) *Attorney, Agent, or Firm* — Hannah M. Tien

(57) ABSTRACT

The present invention relates to a method for alleviating pain in a subject in need thereof, which comprises administering an effective amount of piscidin (PCD) peptide and a pharmaceutically acceptable carrier to the subject.

13 Claims, 13 Drawing Sheets
(7 of 13 Drawing Sheet(s) Filed in Color)

(A)

(B)

(C)

(D)

(A)

(B)

(C)

SEQUENCE LISTING

```
<160> NUMBER OF SEQ ID NOS: 1

<210> SEQ ID NO 1
<211> LENGTH: 22
<212> TYPE: PRT
<213> ORGANISM: Morone chrysops

<400> SEQUENCE: 1

Phe Phe His His Ile Phe Arg Gly Ile Val His Val Gly Lys Thr Ile
1               5                   10                  15

His Arg Leu Val Thr Gly
            20
```

USE OF PEPTIDE FOR ALLEVIATING PAIN

CROSS-REFERENCES TO RELATED APPLICATIONS

The sequence listing text file, file name 2444-AS-US_ST25 created May 28, 2015, file size 488 bytes, is incorporated herein by reference in its entirely.

BACKGROUND OF THE INVENTION

Field of the Invention

The present invention relates to a method for alleviating pain in a subject in need thereof, which comprises administering an effective amount of piscidin (PCD) peptide and a pharmaceutically acceptable carrier to the subject.

Description of Prior Art

Marine organisms are able to thrive in a pathogenic microbe-rich aquatic environment by virtue of their strong innate immune system, which prevents microbial invasion. Antimicrobial peptides serve as a first line of defense against invading pathogens, and are involved in modulating the host signaling mechanisms of the immune response. Previous studies have shown that several antimicrobial peptides inhibit the formation of nitric oxide by interacting with or affecting nitric oxide synthase; such peptides include caerin, cupiennin, dahlein, frenatin, and citropin. An α-helical antimicrobial peptide, named moronecidin or piscidin (PCD)-1, and is not only cationic, but also amphipathic in nature. PCD-1 exerts antimicrobial effects against fish ectoparasites, and bacterial and fungal pathogens. To the best of our knowledge, no earlier studies on the anti-nociceptive effects of antimicrobial peptides have been reported.

Chronic pain affects 1.5 billion people worldwide, and the 2009 global pain market was estimated to be over US $50 billion. Moreover, previous studies showed that about 20% of the general population suffers from chronic pain, and the prevalence of neuropathic pain is 6.9%. The detailed mechanisms of neuropathic pain remain unclear. Neuropathic pain is a widespread health problem associated with nerve injury, prolonged tissue damage, or injury to the peripheral or central nervous system (CNS); the resulting pain is the result of complex changes occurring at various levels in nociceptive pathways. Patients with neuropathic pain often develop hyperalgesia (an increased response to painful stimuli), allodynia (pain evoked by non-painful stimuli), and spontaneous pain and resistance to opioids and other analgesics, including non-steroidal anti-inflammatory drugs. The current research reported that no available drug treatments are able to relieve all neuropathic pain conditions. Therefore, therapeutic treatments of neuropathic syndromes remain challenging on account of their complex natural history, unclear aetiology, and poor response to drugs. The anti-epileptic drug gabapentin is widely used to treat neuropathic pain, and it effectively relieves allodynia, burning pain, shooting pain, and hyperesthesia. However, gabapentin may have side effects, including withdrawal following an adverse event, dizziness, somnolence, peripheral oedema, and gait disturbances. Hence, recent research into treating pain has focused on screening for safe, specific, and effective analgesic compounds from natural sources to alleviate neuropathic pain.

The relationship of neuropathic pain and PCD-1 is not studied in the previous reports.

SUMMARY OF THE INVENTION

The present invention provides a method for alleviating pain in a subject in need thereof, which comprises administering an effective amount of piscidin (PCD) peptide and a pharmaceutically acceptable carrier to the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 13:
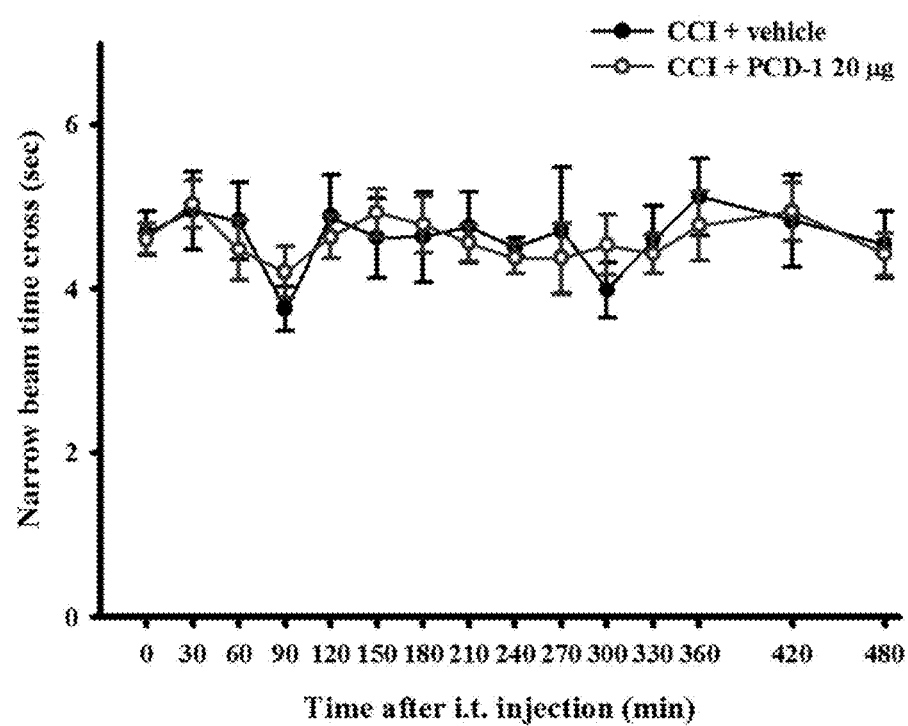
FIG. 13 shows that PCD1 treatment does not affect the locomotory activity of CCI rats in the beam crossing test. Comparison of the latency to initiate crossing and total time to cross the beam between CCI rats+vehicle and CCI rats+PCD-1 (20 μg) is made. No significant differences are observed from 0 to 480 minutes. Groups of 6 rats are used for each treatment.

In the present invention, PCD-1 significantly inhibits up-regulation of the proinflammatory proteins iNOS and COX-2 in macrophages (RAW264.7 cells) and microglias (BV2 cells), and thus this compound may have potential as a complementary treatment to the use of analgesics. The use of peptides, such as PCD-1, is unlikely to induce habituation, as peptides have a short half-life in serum. Furthermore, PCD-1 possesses the properties of an anesthetic compound; injection of PCD-1 significantly inhibits CCI-induced nociceptive behaviors, such as thermal hyperalgesia, mechanical allodynia, cold allodynia, and weight-bearing deficits. Importantly, treatment with PCD-1 does not affect locomotor function in rats (FIG. 13), and nor does it result in any obvious alterations of external behavior. In summary, the mechanisms underlying the anti-nociceptive effects of i.t.-administered PCD-1 in neuropathy may include attenuation of spinal neuroinflammation (microglial and astrocytic activation and up-regulation of IL-1β), attenuation of phospho-mTOR up-regulation in astrocytes, and attenuation of TGF-β1 down-regulation in astrocytes and neuronal cells. The present invention demonstrates that PCD-1 has anti-inflammatory and analgesic properties in both in vitro and in vivo inflammatory models, and thus PCD-1 is the first antimicrobial peptide to be identified as a potential candidate for future development as an anesthetic.

As used herein, "a" or "an" may mean one or more. As used herein in the claim(s), when used in conjunction with the word "comprising", the words "a" or "an" may mean one or more than one.

The present invention provides a method for alleviating pain in a subject in need thereof, wherein the method comprises administering an effective amount of piscidin (PCD) peptide and a pharmaceutically acceptable carrier to the subject.

The piscidin (PCD) peptide is an antimicrobial peptide. The term "piscidin" is referred to Jorge A. Masso-Silva et al.

("Antimicrobial Peptides from Fish", *Pharmaceuticals* 2014, 7, 265-310), which is herein incorporated by reference. In a preferred embodiment, the piscidin (PCD) peptide is a PCD-1 peptide. In a more preferred embodiment, the peptide sequence of the PCD-1 peptide comprises a SEQ ID NO: 1.

The term "alleviating pain" refers to pharmacologic measures that lead to the amelioration of the symptom. Such alleviating pain is sufficient to eliminate or significantly reduce pain or the effects of pain. More specifically, such pharmacological measures include the administration of the mixture described herein to a subject either topically or orally to ameliorate or relieve pain.

The present invention may be used to treat, alleviate, ameliorate, relieve, delay onset of, inhibit progression of, reduce severity of, and/or reduce incidence of one or more symptoms or features of a pain and/or a condition induced by the pain. In a preferred embodiment, the method of the present invention further treats pain.

As used herein, the term "pain" refers to acute and chronic pain, including pain caused by trauma or inflammation such as back pain, toothache, headache, and menstrual cramps, sore throat, fever, and rheumatic pain such as joint pain, gouty arthritis, ankylosing spondylitis, rheumatoid arthritis, and pain associated with systemic connective tissue disorders, cancer, neuropathy and referred pain. In a preferred embodiment, the pain is a chronic pain.

In another embodiment, the pain is a neuropathic pain. In a preferred embodiment, the pain is caused by a neuroinflammation.

The neuroinflammation causes the neuropathic pain. In neuropathy models, iNOS and COX-2 expression are upregulated in microglia and astrocytes. The induction of iNOS in microglia, astrocytes, and neuronal cells in the spinal cord correlates with thermal hyperalgesia. Therefore, the PCD peptide or PCD-1 peptide inhibits the expression level of inflammatory proteins to reduce pain. The inflammatory proteins include but are not limited to a clooxygenase-2 (COX-2) and an inducible nitric oxide synthase (iNOS). In one embodiment, the PCD peptide inhibits the neuroinflammation. In another embodiment, the PCD peptide inhibits the expression level of the inflammatory protein. In a preferred embodiment, the PCD peptide inhibits the expression level of COX-2. In a more preferred embodiment, the PCD peptide inhibits the expression level of iNOS.

As used herein, the "expression level" comprises the expression level of gene, RNA and protein.

In one embodiment, the subject is an animal. Preferably, the subject is a mammal. More preferably, the subject is a human.

A "effective amount" is an amount effective to prevent, lower, stop or reverse the development of, or to partially or totally alleviate the existing symptoms of a particular condition for which the subject is being treated.

In one embodiment, the effective amount is in a range of from about 0.1 µg to about 100 µg. In a preferred embodiment, the effective amount is in a range of from about 1 µg to about 50 µg. In a more preferred embodiment, the effective amount is in a range of from about 10 µg to about 30 µg.

As used herein, the term "pharmaceutically acceptable carrier" is determined in part by the particular composition being administered, as well as by the particular method used to administer the composition. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a subject. The preparation of an aqueous composition that contains a protein as an active ingredient is well understood in the art. Typically, such compositions are prepared as injectables, either as liquid solutions or suspensions; solid forms suitable for dissolving or suspending in liquid prior to injection can also be prepared.

The pharmaceutically acceptable carrier and the PCD peptide are administered to the subject by many routes and in many regimens that are well known to those in the art. In some embodiments, the pharmaceutically acceptable carriers and the PCD peptide are administered intravenously, intramuscularly, subcutaneously, topically, orally, or by inhalation. Through the digestive system and circulatory system, it will be delivered to target locations.

The pharmaceutically acceptable carriers and the PCD peptide may be formulated for administration via sterile aqueous solution or dispersion, aqueous suspension, oil emulsion, water in oil emulsion, site-specific emulsion, long-residence emulsion, sticky-emulsion, microemulsion, nanoemulsion, liposomes, microparticles, microspheres, nanospheres, nanoparticles, minipumps, and with various natural or synthetic polymers that allow for sustained release. The pharmaceutically acceptable carriers and the PCD peptide may also be formulated into aerosols, tablets, pills, sterile powders, suppositories, lotions, creams, ointments, pastes, gels, hydrogels, sustained-delivery devices, or other formulations used in drug delivery.

The subject with pain shows signs of glial activation in a nervous system that modulates pain. Glial activation is accompanied by many cellular responses, which include the production and release of substances (such as so-called 'pro-inflammatory cytokines') that can sensitize the pain pathways in the nervous system. The types of glia cell comprise microglia and macroglia, such as astrocytes, oligodendrocytes and schwann cells. In one embodiment, the PCD peptide decreases the activation of glia cells. In a preferred embodiment, the PCD peptide decreases the activation of microglias. In a preferred embodiment, the PCD peptide decreases the activation of astrocytes.

Activation of spinal mammalian target of rapamycin (mTOR) is required for neuropathy-induced pain hypersensitivity; and phosphorylation of Ser-2448 of mTOR is a biomarker for the activation status of mTOR. The inhibition of mTOR can reduce neuroinflammation. In addition, the IL-1β is a proinflammatory factor. Therefore, the factors that are up-regulated by the inflammatory response comprise IL-1β and phospho-mTOR. Thus, the PCD peptide (or PCD-1 peptide) exerts an analgesic or anti-nociceptive effect through inhibition of the inflammatory response. In an embodiment, the PCD peptide inhibits the up-regulation of the expression level of the phospho-mTOR or IL-1β. In a preferred embodiment, the PCD peptide decreases the expression level of phospho-mTOR. In a more preferred embodiment, the PCD peptide decreases the expression level of IL-1β.

The PCD peptide (or PCD-1 peptide) has anti-neuroinflammatory effects that have been implicated in the subject with peripheral neuropathy. The PCD peptide can attenuate down-regulation of factors (e.g. transforming growth factor beta1 (TGF-β1)) that exerts the anti-neuroinflammatory effects, such as suppressing activation of microglias and astrocytes. In one embodiment, the PCD peptide increases the expression level of TGF-β1.

The present invention further is used to prepare an anesthetic, an analgesic or an anti-inflammatory agent. The pain and/or inflammation may for example be due to chronic conditions including rheumatoid arthritis, osteoarthritis, a spinal disc herniation (e.g., sciatica), carpal/tarsal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, spondilothesis, stenosis, discogenic back pain, and joint pain or the like. An anesthetic is a drug that causes anesthesia, which relieves pain without eliminating sensation. The analgesic refers to an agent or compound that can reduce, relieve or eliminate pain. The phrase "anti-inflammatory agent" refers to an agent or compound that has anti-inflammatory effects. These agents may remedy pain by reducing inflammation.

EXAMPLES

The examples below are non-limiting and are merely representative of various aspects and features of the present invention.

Example 1

Peptide

The peptide sequence of Piscidin-1 (PCD-1) is SEQ ID NO: 1 (FFHHIFRGIVHVGKTIHRLVTG). PCD-1 was synthesized and purified to a grade of >95% by GL Biochemistry (Shanghai, China). The molecular mass and purity was determined to be >95% by high-pressure liquid chromatography (HPLC). Synthetic peptides were dissolved in sterile deionized water or PBS buffer for the experiments.

Data and Statistical Analysis

All data are shown as means±standard error of the mean (SEM). For statistical analyses, differences between groups were calculated using one-way analysis of variance (ANOVA), followed by the Student-Newman-Keuls post hoc test for comparison of multiple groups. The present invention defined statistical significance as $p<0.05$.

Example 2

Anti-Inflammatory and Anti-Neuroinflammatory Activity Assays (1) Method:

Anti-inflammatory and anti-neuroinflammatory activity assays were performed by the following steps. Murine RAW 264.7 macrophages were treated with lipopolysaccharide (LPS) (0.01 µg/ml). Experimental groups were pre-treated with different PCD-1 concentrations (2.5, 5, or 10 µg/ml) for 10 minutes, and then treated with LPS for 16 hours. Murine microglial BV2 cells were treated with different concentrations of PCD-1 (2.5, 5, or 10 µg/ml) for 10 minutes, and then treated with LPS for 16 hours. Cells were washed with ice-cold PBS, and then lysed with ice-cold lysis buffer (pH 7.5, 1 µg/ml aprotinin, 50 mM Tris, 150 mM NaCl, 100 µg/ml phenylmethylsulfonyl fluoride, 1% Triton X-100). Lysates were centrifuged at 20,000×g for 60 min at 4° C., and the supernatant was retained for Western blotting analysis of inducible nitric oxide synthase (iNOS) and cyclooxygenase-2 (COX-2). Protein concentrations in the supernatant were determined using the DC protein assay kit (Bio-Rad, Hercules, Calif., USA). Each sample was then added to an equal volume of sample buffer (10% glycerol, 2% 2-mercaptoethanol, 0.1% bromophenol blue, 50 mM Tris-HCl, pH 7.2, and 2% sodium dodecyl sulfate (SDS)). Proteins were separated by electrophoresis on a tricine SDS-polyacrylamide gel at 150 V for 90 minutes, and the proteins were then transferred to a polyvinylidene difluoride membrane (PVDF membrane; Immobilon-P, Millipore, 0.45-µM pore size) with transfer buffer (380 mM glycine, 1% SDS, 50 mM Tris-HCl, 20% methanol) at 125 mA overnight at 4° C. PVDF membranes were blocked for 1 h at room temperature with 5% non-fat dry milk in Tris-buffered saline (TTBS; 0.1% Tween 20, 137 mM NaCl, 20 mM Tris-HCl, pH 7.4), and then incubated with antibodies against iNOS (1:1000 dilution; BD Pharmingen, San Diego, Calif., USA; catalog no. 6103322; polyclonal antibody) or COX-2 (1:1000 dilution; Cayman Chemical, Ann Arbor, Mich., USA; catalog no. 160106; polyclonal antibody) for 180 min at room temperature. Immunoreactive bands against iNOS (~135 kDa) and COX-2 (~70 kDa) proteins were visualized using enhanced chemiluminescence (ECL kit; Millipore), and photographed using the UVP BioChemi imaging system (UVP LLC, Upland, Calif., USA). Relative densitometric quantification of the immunoreactive bands was performed using LabWorks 4.0 software (UVP LLC, Upland, Calif., USA), and relative variations between the bands of different groups were calculated using the same image. Intensities of each band for the LPS only control were set at 100%. Additionally, The present invention reprobed the PVDF membranes with an anti-β-actin antibody (1:2500 dilution; catalog no. A5441; Sigma Co., Ltd., St Louis, Mo., USA; monoclonal mouse antibody); β-actin was used as the loading control.

Figure 1:
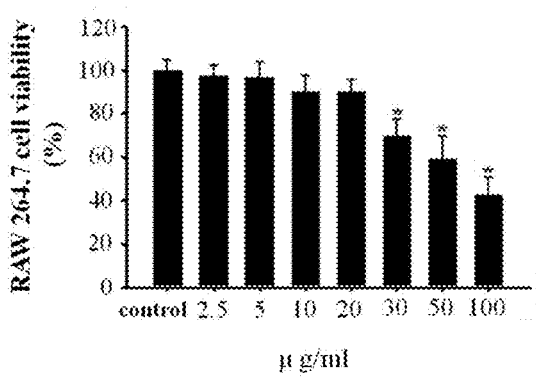
FIG. 1 shows that PCD-1 decreases LPS-mediated induction of iNOS and COX-2 in RAW264.7 cells. (A) RAW264.7 cells are treated with the indicated doses of PCD-1 for 24 h, and cell viability is then measured by Alamar blue assay to assess cytotoxicity. (B) Western blot against iNOS and COX-2. (C) Relative density of iNOS in immunoblots. (D) Relative density of COX-2 in immunoblots. Both iNOS and COX-2 are significantly inhibited by PCD-1 in RAW264.7 cells. Experiments are repeated three times. *, $p<0.05$ compared with the LPS-stimulated control group.
Figure 1:
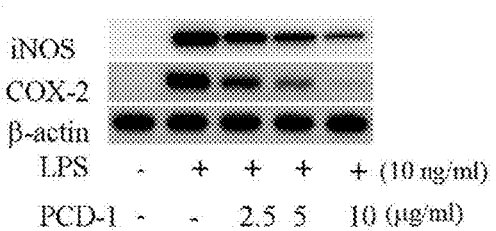
Figure 1:
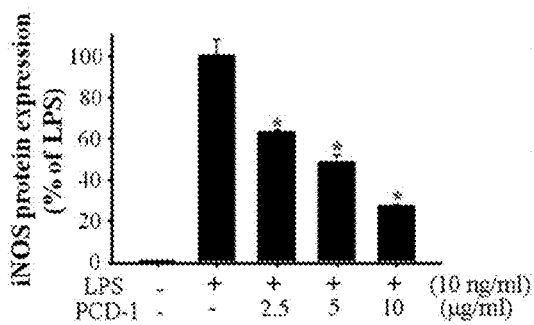
Figure 1:
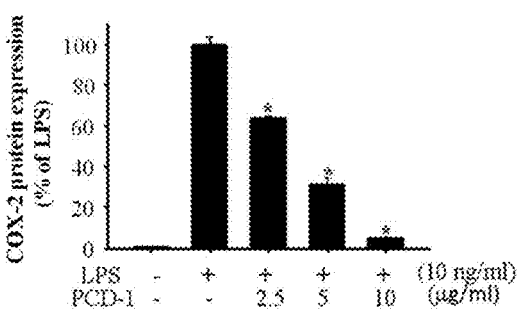
Figure 2:
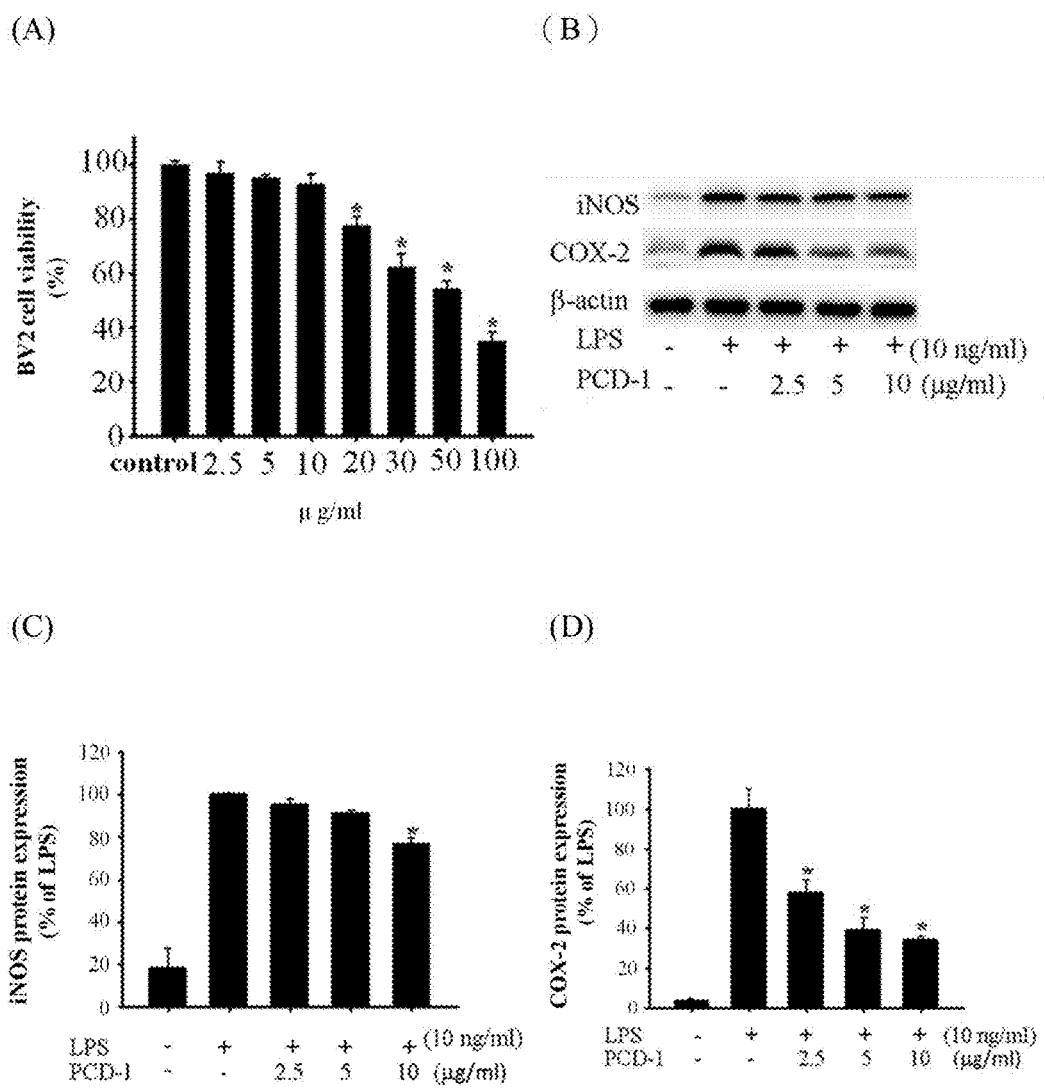
FIG. 2 shows that PCD-1 decreases LPS-mediated induction of iNOS and COX-2 in BV2 cells. (A) BV2 microglia cells are treated with the indicated doses of PCD-1 for 24 h, and cell viability is measured by Alamar blue assay to assess cytotoxicity. (B) Western blot against iNOS and COX2. (C) Relative density of iNOS in immunoblots. (D) Relative density of COX-2 in immunoblots. Both iNOS and COX-2 are significantly inhibited by PCD-1 in BV2 cells. Experiments are repeated three times. *, $p<0.05$ compared with the LPS-stimulated control group.

(2) Results:

PCD-1 Suppressed Up-Regulation of iNOS and COX-2 Expression in LPS-Treated RAW264.7 and Microglial Cells Inhibition of iNOS and COX-2 induced anti-nociceptive behaviors. In order to investigate regulation of iNOS and COX-2 by PCD-1, mouse macrophage and immune cells were treated with non-cytotoxic doses of PCD-1, and the effects on protein expression were examined. Proliferation of RAW264.7 cells was unaffected by treatment with up to 20 g/ml PCD-1 for 24 h (FIG. 1A). As such, non-cytotoxic doses of 0 to 10 g/ml of PCD-1 were used in subsequent anti-inflammatory activity assays. Expression levels of iNOS and COX-2 were examined by Western blotting (FIG. 1B); the relative intensities of expression were shown in FIGS. 1 (C) and 1 (D). Treatment with LPS alone resulted in up-regulation of iNOS and COX-2 expression, whereas the addition of PCD-1 suppressed expression in a dose-dependent manner (FIG. 1 (B)-(D)). Next, the effect of PCD-1 on the expression of iNOS and COX-2 was examined in the microglial cell line BV2, to mimic the effect on residential immune cells in the CNS. Similar to the observations in RAW264.7 cells, the LPS-induced up-regulation of iNOS and COX-2 was attenuated in a dose-dependent manner by PCD-1 in BV2 cells (FIG. 2).

Example 3

Rat Model of Chronic Constriction Injury and Test Thereof

Method:

(1) Chronic Constriction Injury (CCI) and Implantation of i.t. Catheters

The rat model of chronic constriction injury (CCI) was performed by following the previous reports or research. Implantation of i.t. catheters in rats was performed. The i.t. catheters (PE5 tubes: 9-cm long, 0.008-inch inner diameter, 0.014-inch outer diameter; Spectranetics, Colorado Springs, Colo., USA) were inserted via the atlanto-occipital membrane into the i.t. space at the level of the lumbar enlargement of the spinal cord, and externalized and fixed to the cranial aspect of the head. Five days after i.t. catheterization, CCI or mononeuropathy was induced by following a previous report. The 5-mm-long nerve segment of right sciatic nerve at the mid-thigh level was isolated from the surrounding tissues. Four ligatures (4-0 chromic gut) were loosely tied around the sciatic nerve with 1-mm intervals, and the wound was closed with sutures.

(2) Pain Behavior Assay (a) Thermal Hyperalgesia Test

Thermal hyperalgesia was examined using an IITC analgesiometer (IITC Inc., Woodland Hills, Calif., USA). Rats were placed in plastic cages on top of an elevated glass plate, and low intensity radiant heat (active intensity=25) was applied until rats showed positive signs of pain (licking or withdrawal). Paw withdrawal latency (PWL) in seconds was measured with a cutoff time of 30 seconds. PWL was recorded at 30, 60, 90, 120, 150, and 180 minutes after PCD-1 or gabapentin injection. PWL (s) was transformed to a percentage of the maximum possible effect (% MPE) using the following formula: % MPE=(post-drug latency−baseline)/(cutoff−baseline)×100%, where the post-drug latency was the response measured at 0, 30, 60, 90, 120, 150, or 180 minutes after injection of PCD-1, gabapentin, or vehicle. The baseline was the response measured immediately prior to i.t. injection, and the cutoff time was 30 seconds.

(b) Mechanical Allodynia Test

Mechanical allodynia was measured by assessing paw withdrawal threshold (PWT) in grams using calibrated Von Frey filaments (Stoelting, Wood Dale, Ill., USA). Rats were placed in cages on top of an elevated metal mesh floor, and a series of von Frey filaments of logarithmically incremental stiffness were applied by Chaplan's up-down method at the midplantar region of the hindpaw to identify the filament closest to the threshold of pain response.

(c) Cold Allodynia Test

After placing rats in cages on an elevated metal mesh floor, 25 μl of acetone was applied at the center of the plantar surface of a hindpaw, and the cold allodynia response (acetone response score; in point) of the rat was monitored for 1 minute after acetone stimulus. The acetone response scale was modified from a 4-point scale to a 6-point scale, as follows: 0, repeated flicking with persistent licking within 2 seconds of stimulus; 1, prolonged withdrawal or repeated flicking within 2 seconds of stimulus; 2, quick and more violent withdrawal, flick, or stamp within 2 seconds of stimulus; 3, quick withdrawal, flick, or stamp within 2 seconds of stimulus; 4, withdrawal, flick, or stamp after 2 seconds of stimulus; 5, no response. Finally, the four individual acetone response scores of each rat were summed. The minimum possible total score was 0 points, and the maximum possible total score was 20 points.

(d) Weight-Bearing Test

Rats were placed on an incapacitance tester (Singa Technology Corporation, Taiwan) so that the hind paws were centered on the two force transducers, enabling the weight distribution between the rat's hind limbs to be measured. Hind paw weight distribution was expressed in grams by calculating the difference between the normal limb and the affected limb measured at the same time point.

(e) Narrow Beam Test

The narrow beam used in the present invention was a wooden beam 80 cm in length and 2.5 cm in width, suspended 100 cm from the ground by wooden supports at either end. Foam padding (1 m wide and approximately 12 cm thick) was placed beneath the beam to prevent injury to the rat in case of a fall. The cutoff time to cross the beam was 15 seconds for each rat. Rats were pre-trained before the test.

(3) Immunohistofluorescence Analysis

Spinal tissue was collected from naïve rats, CCI rats treated with i.t. vehicle, or CCI rats treated with i.t. PCD-1 (20 g) at 30, 90, or 180 minutes after drug treatment. Tissue sections (10 μm) were incubated overnight at 4° C. with anti-OX42, anti-GFAP, anti-phospho-mTOR, anti-IL-1β, or anti-TGF-β1 antibodies. Cell types were identified based on markers of microglia (OX42), astrocytes (GFAP), or neurons (NeuN). Sections were then incubated for 40 minutes at room temperature with Alexa Fluor 488-labeled chicken anti-mouse IgG antibody (1:400 dilution, cat. A-21200; Molecular Probes, Eugene, Oreg., USA; green fluorescence), DyLight 549-conjugated donkey anti-rabbit IgG antibody (1:400 dilution, cat. 711-506-152; Jackson ImmunoResearch Laboratories Inc., West Grove, Pa., USA; red fluorescence), or Alexa Fluor 488-conjugated donkey anti-goat IgG antibody (1:400 dilution, cat. 705-546-147; Jackson ImmunoResearch Laboratories Inc., West Grove, Pa., USA; green fluorescence). This enabled the detection of phospho-mTOR or TGF-β1 as pseudo-green signals. For double immunofluorescent staining, spinal sections were incubated with a mixture of anti-OX42 and anti-phospho-mTOR, anti-GFAP and anti-phospho-mTOR, anti-NeuN and anti-p-mTOR, anti-OX42 and anti-TGF-β1, anti-GFAP and anti-TGF-β1, or anti-NeuN and anti-TGF-β1 antibodies overnight at 4° C., followed by incubation with a mixture of Alexa Fluor 488 conjugated and DyLight 549-conjugated secondary antibody for 40 minutes at room temperature. Four spinal sections were randomly selected and scanned using a Leica DM-6000 CS fluorescence microscope (Leica Instruments Inc., Wetzlar, Germany), and the images were captured with a SPOT Xplorer digital camera (Diagnostic Instruments, Inc., Sterling Heights, Mich., USA). To quantify immunofluorescence staining, every fourth section from a series of lumbar spinal cord sections was selected, and four successive sections were measured. The images were quantified using Image J software (National Institutes of Health, Bethesda, Md., USA) by an observer unaware of the experimental conditions. Pixel values of the immunoreactive-positive area in the image of the dorsal horn of the spinal cord were measured. Immunohistochemical data were expressed as the percentage change compared with data from untreated control animals, which were considered to be 100%.

Results:

(1) PCD-1 Had Dose-Dependent Anti-Thermal Hyperalgesia Effects in CCI Rats

Figure 3:
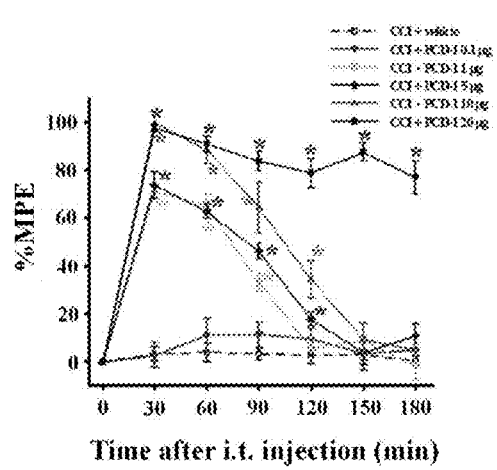
FIG. 3 shows that PCD-1 has similar anti-thermal hyperalgesia effects to those of gabapentin in CCI rats. CCI rats are i.t. administered with (A) PCD-1 (0, 0.1, 1, 5, 10, or 20 μg) or (B) gabapentin (0, 1, 5, 10, or 20 μg). The dose-response curves from the peak effects of % MPE for anti-thermal hyperalgesia are shown. Groups of 6 rats are used for each treatment. (C) The median effective doses (ED50) of PCD-1 or gabapentin are determined from the standard curves. The ED50 values for anti-thermal hyperalgesia in CCI rats of PCD-1 and gabapentin are 9.5±3.2 μg, and 2.3±1.5 μg, respectively *, $p<0.05$, compared with CCI+vehicle at the indicated time points.
Figure 3:
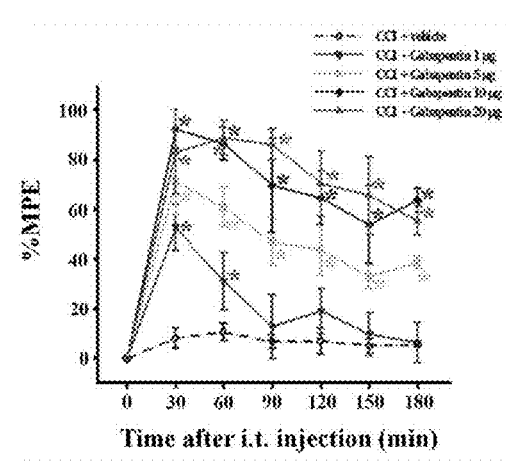
Figure 3:
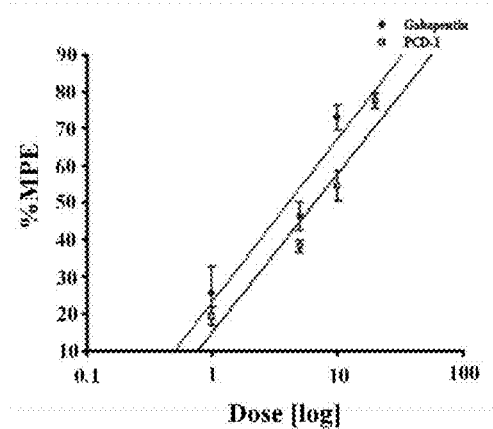

Paw withdrawal latency (PWL) was subsequently examined at various time points from 0 to 180 minutes after i.t. administration of 0, 0.1, 1, 5, 10, or 20 μg of PCD-1. PCD-1 treatment resulted in a dose-dependent increase in the % maximum possible effect (MPE) for anti-thermal hyperalgesia in CCI rats (FIG. 3A). A dose of 20 μg of PCD-1 resulted in a significant increase in anti-thermal hyperalgesia at all the time points examined (FIG. 3A), and this dose was used for further experiments. The effects of PCD-1 treatment on thermal hyperalgesia in CCI rats were similar to those of gabapentin, a drug used widely against neuropathy pain (FIG. 3B). The median effective doses (ED50) for anti-thermal hyperalgesia of PCD-1 and gabapentin were 9.5±3.2 µg and 2.3±1.5 µg, respectively (FIG. 3 (C)).

Figure 4:
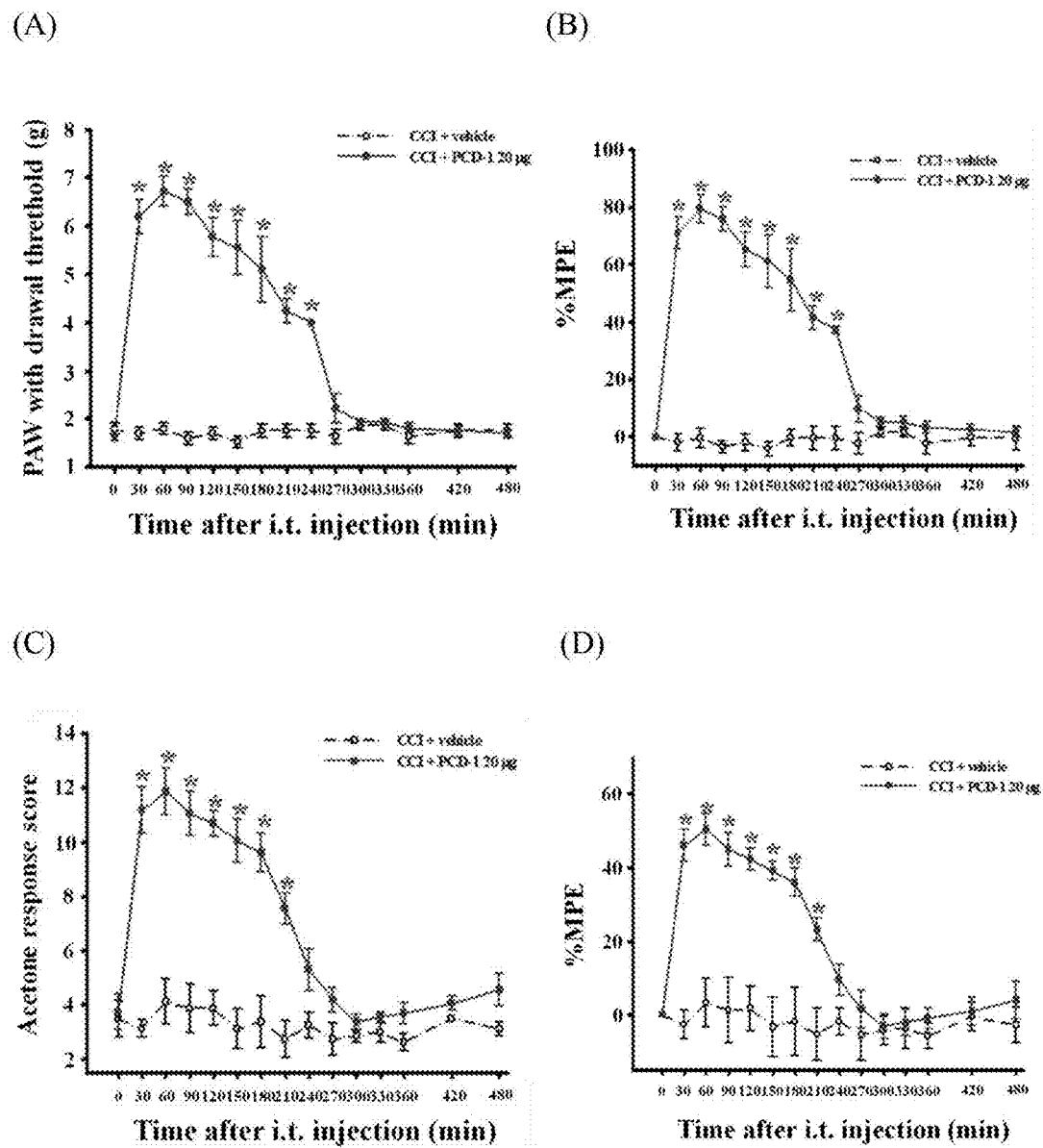
FIG. 4 shows that PCD-1 has anti-mechanical allodynia and anti-cold allodynia effects in CCI rats. Effects of PCD-1 (20 μg) on CCI-induced mechanical allodynia are shown in (A) and (B) and cold allodynia are shown in (C) and (D). Anti-nociception data shown in (A) and (C) are expressed as % MPE shown in (B) and (D) after PCD-1 injection. In CCI rats, i.t. administration of PCD-1 has anti-mechanical allodynia effects from 30 to 240 minutes and anti-cold allodynia effects from 30 to 210 minutes. Groups of 6 rats are used for each treatment. *, $p<0.05$, compared with CCI+vehicle at the indicated time points.
Figure 5:
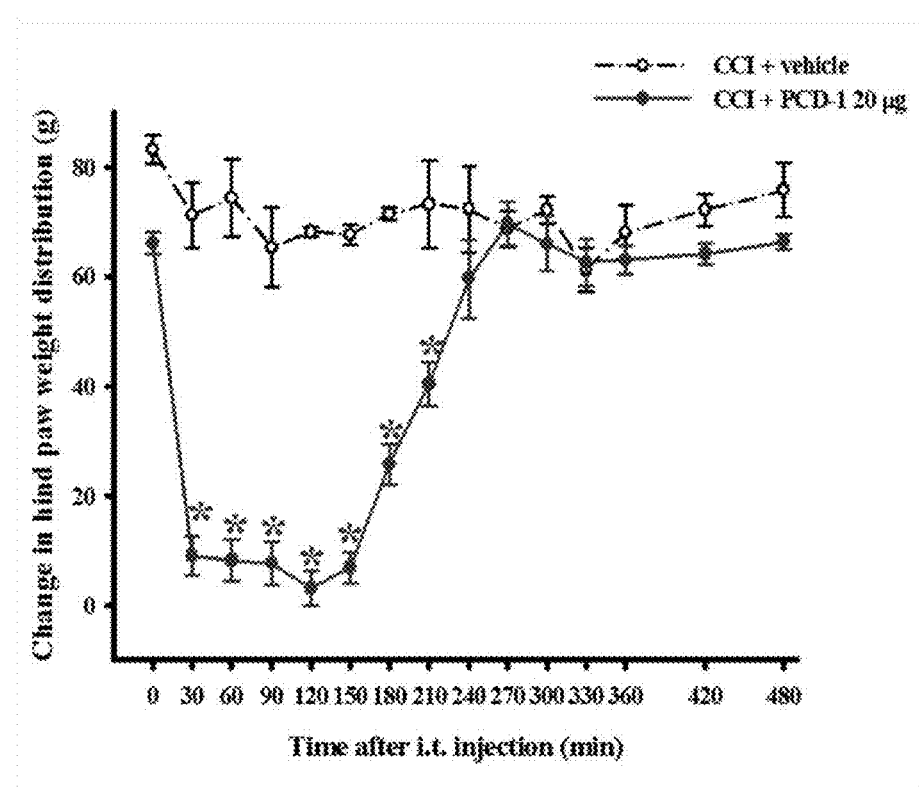
FIG. 5 shows that PCD-1 has anti-weight-bearing deficit effects in CCI rats. In CCI rats, i.t. PCD-1 (20 μg) administration exerts anti-weight-bearing deficits from 30 to 210 minutes. Groups of 6 rats are used for each treatment. *, $p<0.05$, compared with CCI+vehicle at the indicated time points.

(2) PCD-1 Had Anti-Mechanical Allodynia, Anti-Cold Allodynia, and Anti-Weight-Bearing Deficit Properties in CCI Rats In CCI rats treated with vehicle, the paw withdrawal threshold (PWT) remained unchanged at all time points (FIG. 4 (A)). As compared to the controls, CCI rats injected with PCD-1 exhibited a significant increase in PWT after 30 minutes; PWT peaked at 60 minutes, and remained significantly greater than in the control for up to 240 minutes after the commencement of treatment (FIG. 4 (A), (B)). Next, the rats were subjected to cold stimuli to measure cold allodynia. The cold allodynia response of vehicle-treated CCI rats was close to the baseline value at all time points, whereas PCD-1-treated CCI rats showed increased anti-cold allodynia at 30 minutes; the anti-cold allodynia effect peaked at 60 minutes, and remained high for up to 210 minutes post-injection with PCD-1 (FIGS. 4C and 4D). In addition, hind paw weight bearing distribution was greatly reduced in CCI rats between 30 and 210 minutes post-injection with PCD-1, as measured using an incapacitance tester (FIG. 5).

(3) PCD-1 Decreased CCI-Induced Activation of Microglia and Astrocytes in Rats

Figure 6:
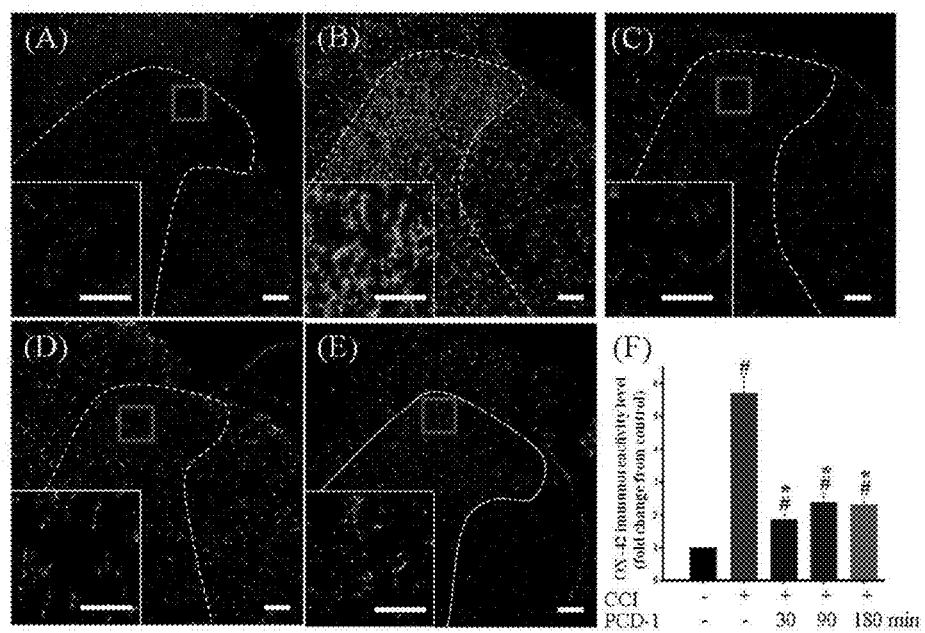
FIG. 6 shows that PCD-1 treatment suppresses CCI-induced activation of microglia. CCI rats are i.t. injected with 20 μg of PCD-1 or vehicle control. Spinal microglia activation is observed by immunohistochemistry using OX42 marker. (A) Control rat, (B) CCI rat, (C) CCI+PCD-1 rat at 30 minutes, (D) CCI+PCD-1 rat at 90 minutes, (E) CCI+PCD-1 rat at 180 minutes. (F) Quantification of OX-42 immunoreactivity reveals that PCD-1 significantly, but not completely, inhibits CCI-induced microglial activation in the dorsal horn of the spinal cord. Groups of 6 rats are used for each treatment. Scale bar=50 μm. #, p<0.05 compared with the control; *, p<0.05 compared with the CCI group.
Figure 7:
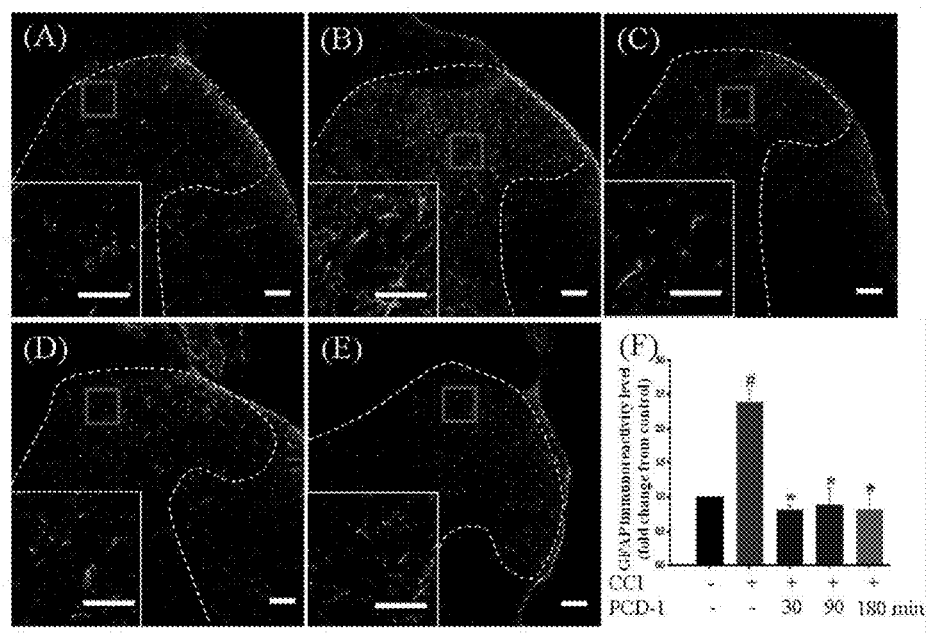
FIG. 7 shows that PCD-1 suppresses CCI-induced activation of astrocytes. CCI rats are i.t. injected with 20 μg of PCD-1 or vehicle control. Spinal astrocytic activation is observed by immunohistochemistry using GFAP marker. (A) Control rat, (B) CCI rat, (C) CCI+PCD-1 at 30 minutes, (D) CCI+PCD-1 rat at 90 minutes, (E) CCI+PCD-1 rat at 180 minutes. (F) Quantification of GFAP immunoreactivity reveals that PCD-1 significantly inhibits CCI-induced astrocyte activation in the dorsal horn of the spinal cord. Groups of 6 rats are used for each treatment. Scale bar=50 μm. #, p<0.05 compared with the control; *, p<0.05 compared with the CCI group.

To investigate CNS glial cell activation, spinal cord sections were stained with antibodies specific to markers of microglia (OX42) and astrocytes (GFAP). Compared to control rats (FIG. 6A), CCI rats showed increased activation of microglia (OX42) cells (FIG. 6B). Activation of microglia was also decreased by i.t. administration of PCD-1 in CCI rats at 30, 90, and 180 minutes post-treatment (FIG. 6C-F). In a similar fashion, astrocytes (GFAP) were activated in CCI rats, and such induction was greatly reduced by PCD-1 at 30, 90, and 180 minutes post-treatment (FIG. 7A-F).

(4) PCD-1 Regulated the CCI-Mediated Up-Regulation of IL-1β and Phospho-mTOR, and Down-Regulation of TGF-β1

Figure 8:
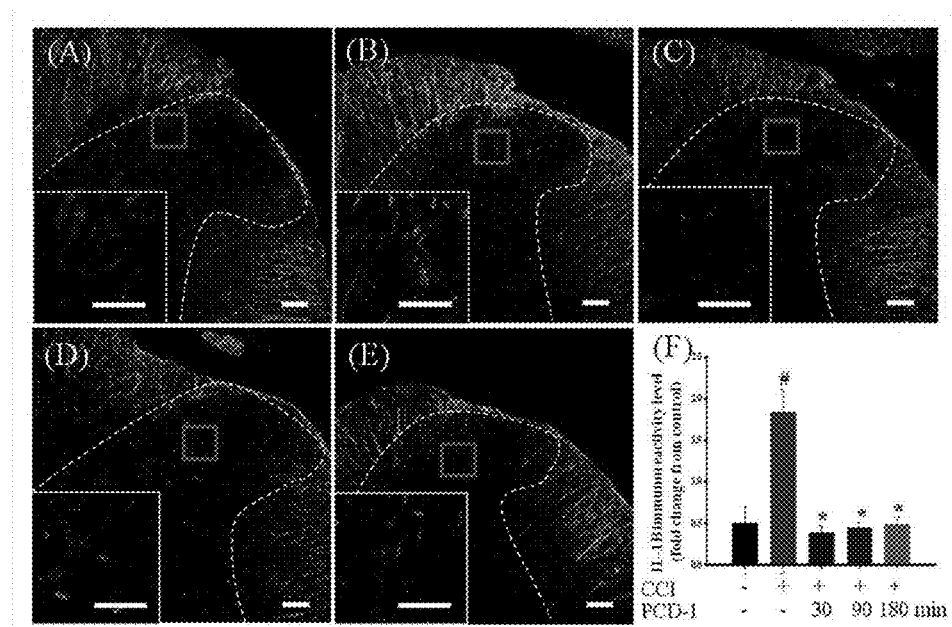
FIG. 8 shows that PCD-1 suppresses CCI-induced activation of IL-1β. CCI rats are i.t. injected with 20 μg of PCD-1 or vehicle control. Spinal IL-1β expression is observed by immunohistochemistry using anti-IL-1β antibody. (A) Control rat, (B) CCI rat, (C) CCI+PCD-1 rat at 30 minutes, (D) CCI+PCD-1 rat at 90 minutes, (E) CCI+PCD-1 rat at 180 minutes. (F) Quantification of IL-1β immunoreactivity reveals that PCD-1 significantly inhibits CCI-induced up-regulation of IL-1β in the dorsal horn of the spinal cord. Groups of 6 rats are used for each treatment. Scale bar=50 μm. #, p<0.05 compared with the control; *, p<0.05 compared with the CCI group.
Figure 9:
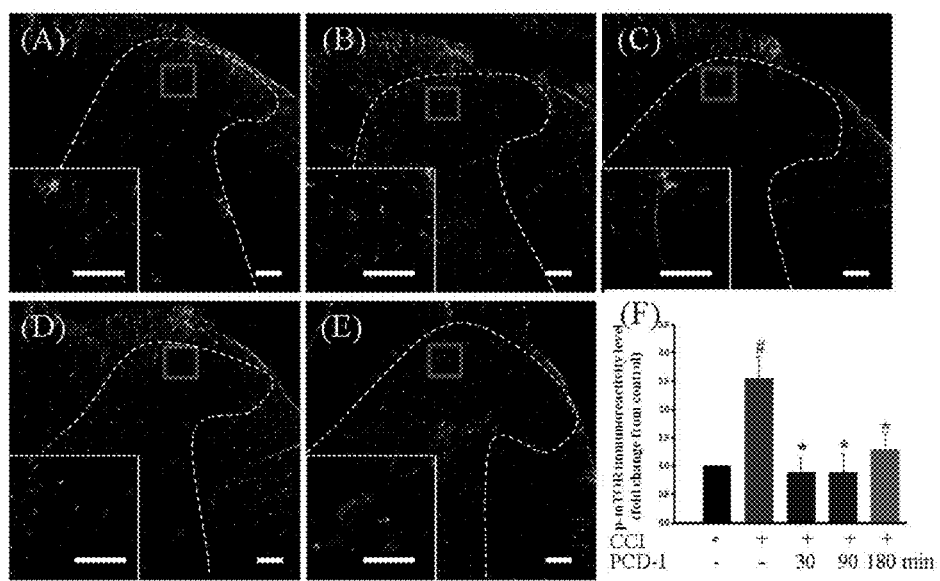
FIG. 9 shows that PCD-1 regulates CCI-induced up-regulation of phospho-mTOR. CCI rats are i.t. injected with 20 μg of PCD-1 or vehicle control. Spinal phospho-mTOR expression is observed by immunohistochemistry using anti-phospho-mTOR antibody. (A) Control rat, (B) CCI rat, (C) CCI+PCD-1 rat at 30 minutes, (D) CCI+PCD-1 rat at 90 minutes, (E) CCI+PCD-1 rat at 180 minutes. (F) Quantification of phospho-mTOR immunoreactivity reveals that PCD-1 significantly inhibits CCI-induced up-regulation of phospho-mTOR in the dorsal horn of the spinal cord. Groups of 6 rats are used for each treatment. Scale bar=50 μm. #, p<0.05 compared with the control; *, p<0.05 compared with the CCI group.
Figure 10:
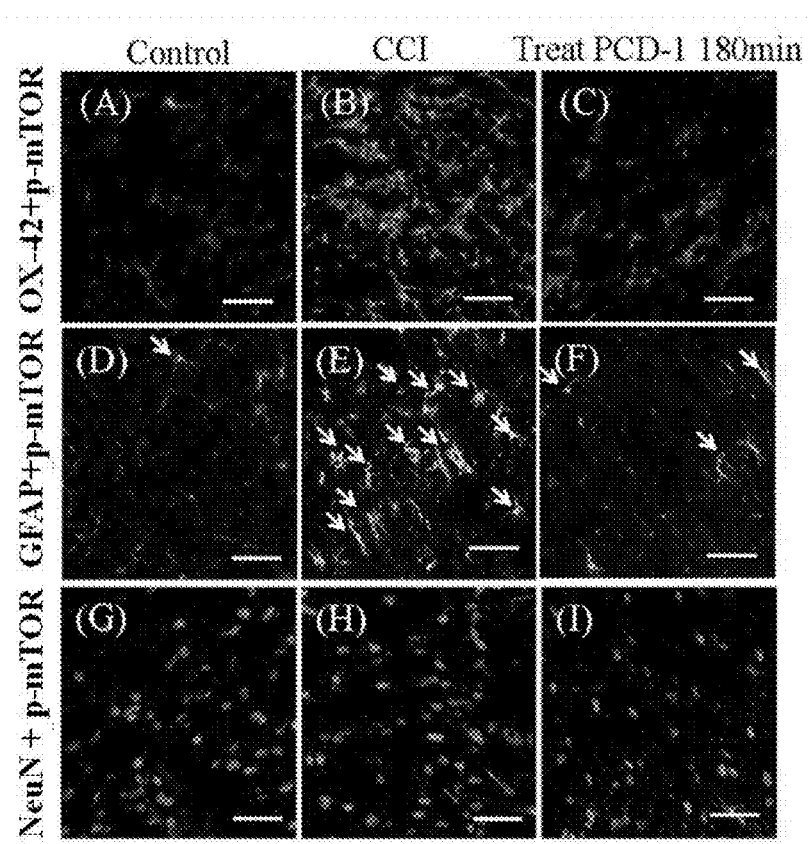
FIG. 10 shows that PCD-1 treatment decreases CCI-induced up-regulation of phospho-mTOR in microglia, astrocytes, and neurons. CCI rats are i.t. injected with 20 μg of PCD-1 or vehicle control. Spinal cord sections are taken at 180 minutes post PCD-1 injection, and co-localization of phospho-mTOR with markers specific for microglia (OX-42, green staining), astrocytes (GFAP, green staining), or neuronal cells (NeuN, green staining) is analyzed. Spinal cord sections are shown for control rats (A), (D), and (G), CCI rats (B), (E), and (H), and CCI rats treated with PCD-1 (C), (E), and (I) at 180 minutes post-treatment. Double immunofluorescent staining reveals that PCD-1 significantly inhibits CCI-induced up-regulation of phospho-mTOR (red staining) in astrocytes. The white arrows indicate colocalization of GFAP with phospho-mTOR; such colocalization in CCI rats is reduced by PCD-1 treatment (F) as compared to vehicle controls (E). Scale bars: 25 μm.
Figure 11:
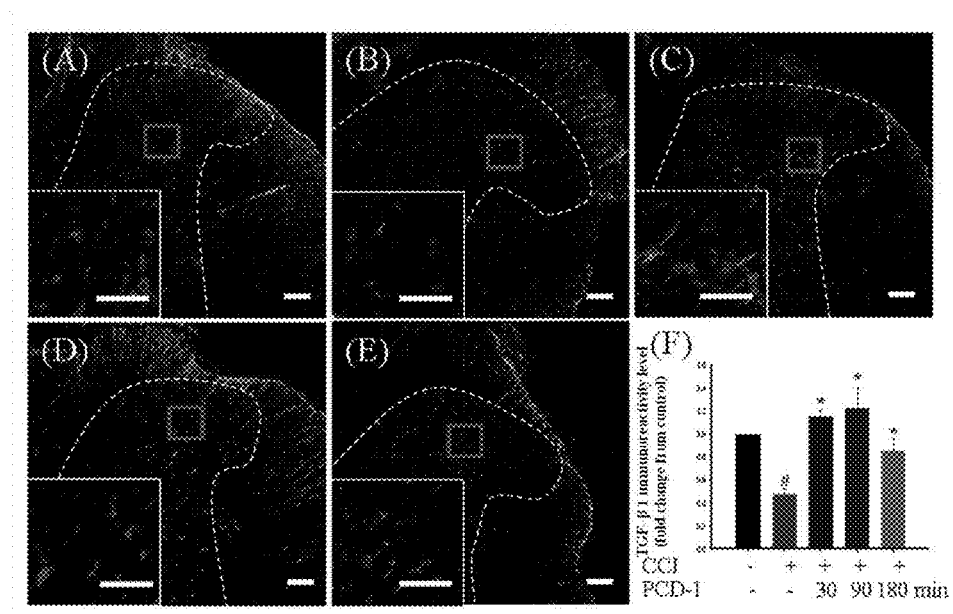
FIG. 11 shows that PCD-1 regulates CCI-induced down-regulation of TGF-β1. CCI rats are i.t. injected with 20 μg of PCD-1 or vehicle control. Spinal TGF-β1 expression is observed by immunohistochemistry using anti-TGF-β1 antibody. (A) Control rat, (B) CCI rat, (C) CCI+PCD-1 rat at 30 minutes, (D) CCI+PCD-1 rat at 90 minutes, (E) CCI+PCD-1 rat at 180 minutes. (F) Quantification of TGF-β1 immunoreactivity reveals that PCD-1 significantly rescues CCI-induced down-regulation of TGF-β1 in the dorsal horn of the spinal cord. Groups of 6 rats are used for each treatment. Scale bar=50 μm. #, p<0.05 compared with the control; *, p<0.05 compared with the CCI group.
Figure 12:
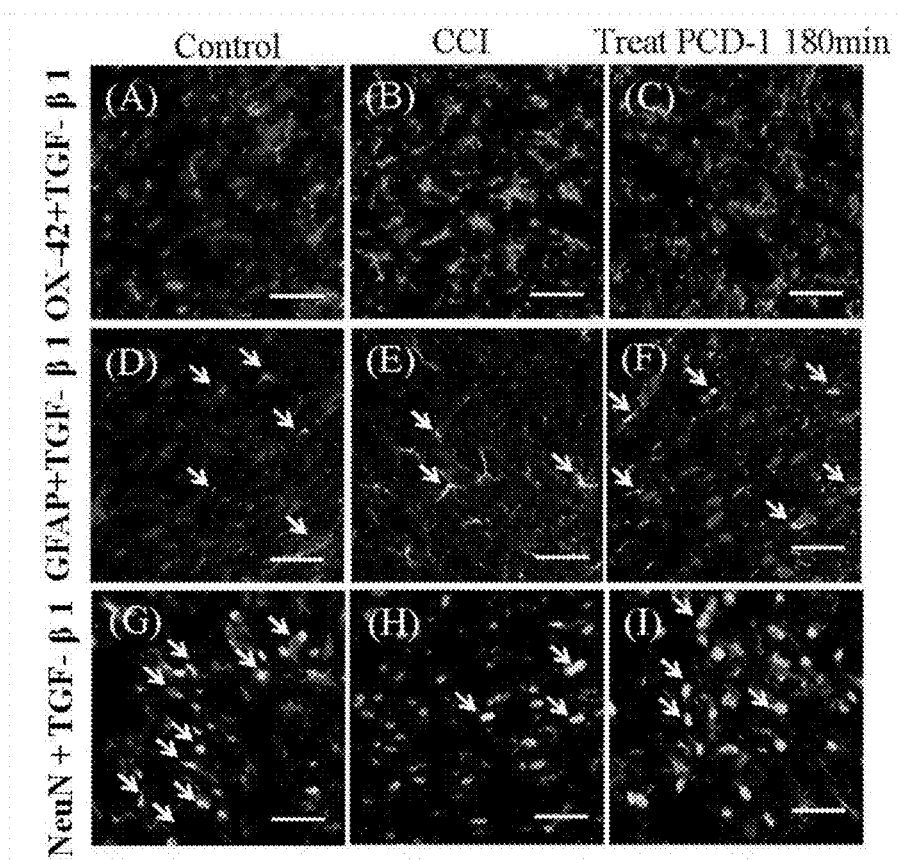
FIG. 12 shows that PCD-1 attenuates CCI-induced down-regulation of TGF-β1 in microglia, astrocytes, and neurons. CCI rats are i.t. injected with 20 μg of PCD-1 or vehicle control. Spinal cord sections are taken at 180 minutes post PCD-1 injection, and co-localization of TGF-β1 with markers specific for microglia (OX-42, green staining), astrocytes (GFAP, green staining), or neuronal cells (NeuN, green staining) is analyzed. Spinal cord sections are shown for control rats (A), (D), and (G), CCI rats (B), (E), and (H), and CCI rats treated with PCD-1 (C), (E), and (I) at 180 minutes post-treatment. Double immunofluorescent staining reveals that PCD-1 significantly inhibits CCI-induced down-regulation of TGF-β1 (red staining) in astrocytes and neuronal cells. The white arrows indicate colocalization of GFAP or NeuN with TGF-β1; such colocalization in CCI rats is increased by PCD-1 treatment (F) and (I) as compared to vehicle controls (E) and (H). Scale bars: 25 μm.

To examine regulation of IL-1β by PCD-1, the expression of IL-1β in spinal cord sections from control and CCI rats was examined by immunohistochemistry. IL-1β expression was higher in CCI rats than in control and PCD-1 (20 µg) treated groups (FIG. 8). The stress-associated protein phospho-mTOR was also up-regulated in CCI rats, and such up-regulation was attenuated by injection of PCD-1 (FIG. 9). Notably, phospho-mTOR was up-regulated by CCI in astrocytes, and this up-regulation was suppressed by PCD-1 (FIG. 10). Another protein associated with neuropathy, TGF-β1, was down-regulated in CCI rats as compared to controls, and this was rescued by PCD-1 treatment (FIG. 11). Finally, up-regulation of TGF-β1 by PCD-1 was observed in astrocytes and neuronal cells of CCI rats (FIG. 12). In addition, the treatment with PCD-1 did not affect locomotor function in rats (FIG. 13), and nor did it result in any obvious alterations of external behavior in the present invention.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for alleviating neuropathic pain in a subject in need thereof, wherein the method comprises administering an effective amount of piscidin (PCD) peptide and a pharmaceutically acceptable carrier to the subject, wherein the PCD peptide is a PCD-1 peptide comprising the amino acid sequence of SEQ ID NO: 1.

2. The method of claim 1, wherein the neuropathic pain is caused by a neuroinflammation.

3. The method of claim 2, wherein the PCD-1 peptide inhibits the neuroinflammation.

4. The method of claim 1, wherein the subject is a human.

5. The method of claim 1, wherein the PCD-1 peptide inhibits expression level of COX-2.

6. The method of claim 1, wherein the PCD-1 peptide inhibits expression level of iNOS.

7. The method of claim 1, wherein the PCD-1 peptide decreases activation of microglias.

8. The method of claim 1, wherein the PCD-1 peptide decreases activation of astrocytes.

9. The method of claim 1, wherein the PCD-1 peptide decreases expression level of IL-1β.

10. The method of claim 1, wherein the PCD-1 peptide decreases expression level of phospho-mTOR.

11. The method of claim 1, wherein the PCD-1 peptide increases expression level of TGF-β1.

12. The method of claim 1, wherein the effective amount is in a range of from about 1 µg to about 50 µg.

13. The method of claim 1, wherein the effective amount is in a range of from about 10 µg to about 30 µg.

* * * * *